United States Patent [19]

Winkelman

[11] Patent Number: 4,789,733

[45] Date of Patent: Dec. 6, 1988

[54] PURIFICATION OF BLOOD COAGULATION FACTOR VIII BY PRECIPITATION WITH SULFATED POLYSACCHARIDES

[75] Inventor: Lowell Winkelman, Oxford, England

[73] Assignee: The Central Blood Laboratories Authority, Borehamwood, England

[21] Appl. No.: 928,178

[22] PCT Filed: Mar. 6, 1986

[86] PCT No.: PCT/GB86/00121

§ 371 Date: Nov. 17, 1986

§ 102(e) Date: Nov. 17, 1986

[87] PCT Pub. No.: WO86/05190

PCT Pub. Date: Sep. 12, 1986

[30] Foreign Application Priority Data

Mar. 7, 1985 [GB] United Kingdom ................ 8505882

[51] Int. Cl.⁴ .............. A61K 35/14; A61K 35/16; C07K 3/28
[52] U.S. Cl. .................... 530/383; 424/101; 514/8
[58] Field of Search .............. 424/101; 530/383; 514/8

[56] References Cited

U.S. PATENT DOCUMENTS

| | | | |
|---|---|---|---|
| 3,803,115 | 4/1974 | Fekete et al. | 530/383 |
| 3,842,061 | 10/1974 | Andersson et al. | 424/101 X |
| 4,022,758 | 5/1977 | Andersson et al. | 530/383 |
| 4,104,266 | 8/1978 | Wickerhauser | 530/383 |
| 4,203,891 | 5/1980 | Rock | 530/383 |
| 4,210,580 | 7/1980 | Amrani | 530/383 |
| 4,278,594 | 7/1981 | Amrani | 424/101 X |
| 4,388,232 | 6/1983 | Eibl et al. | 530/380 X |
| 4,395,396 | 7/1983 | Eibl et al. | 424/101 |
| 4,522,751 | 6/1985 | Linnau et al. | 530/383 |
| 4,578,218 | 3/1986 | Saundry et al. | 424/101 X |
| 4,650,858 | 3/1987 | Rasmussen et al. | 530/383 |
| 4,739,039 | 4/1988 | Vasquez et al. | 530/383 |

OTHER PUBLICATIONS

Biological Abstracts, vol. 63, No. 9, May 1977, 4815 Abstract 48885, Bukurestliev et al.

Primary Examiner—Howard E. Schain
Attorney, Agent, or Firm—Nixon & Vanderhye

[57] ABSTRACT

Efficient precipitation and removal of the proteins fibrinogen and fibronectin from blood plasma fractions, expecially cryoprecipitate, while leaving high yields of blood coagulation factor VIII in the supernatant. This is achieved by the addition of at least 0.15 mg, preferably 0.3–0.9 mg, of a sulphated polysaccharide, especially heparin, per ml of buffered plasma fraction solution while maintaining the temperature of the solution during fibrinogen/fibronectin removal at more than 15° C., preferably 20°–35° C. Lyophilised factor VIII preparation prepared from the factor VIII-rich supernatant product of the invention are suitable for heat treatment at, for example, 70° C. for 24 hours to inactivate blood-born viruses without significant generation of insoluble denatured protein by-products.

23 Claims, No Drawings

PURIFICATION OF BLOOD COAGULATION FACTOR VIII BY PRECIPITATION WITH SULFATED POLYSACCHARIDES

This invention relates to the purification of factor VIII (Antihaemophilic Factor, AHF) from blood plasma concentrates, especially cryoprecipitate.

Blood clotting factor VIII (which is also referred to in this specification as FVIII), is a protein component of blood which has for many years been used to treat individuals suffering from classical haemophilia (haemophilia A), a congenital disease caused by a deficiency or absence of factor VIII in the blood. Until the 1960s treatment of haemophiliacs consisted of transfusing the patient with whole blood or blood plasma. However, in the last 10 to 20 years, factor VIII—enriched plasma protein concentrates have increasingly replaced these whole plasma transfusions and have increased the effectiveness of anti-haemophilia treatment.

The most commercially important of the plasma concentrates currently used are the blood plasma fraction commonly known as cryoprecipitate and purified concentrates prepared from cryoprecipitate. Conventionally, cryoprecipitate is defined as a precipitate, rich in factor VIII, fibrinogen (blood coagulation Factor I) and fibronectin (cold-insoluble globulin, CIg), which is prepared from frozen freshly-prepared human plasma by a low temperature plasma fractionation technique. Typically, deep-frozen plasma is softened to $-5°$ C. to $-15°$ C., and then warmed slowly under efficient manual or mechanical stirring to a temperature of not more than about $3°$ C. Under these conditions the frozen plasma partially thaws to yield a liquid phase and a solid phase, and it is this solid phase which is recovered by centrifugation as commercially valuable cryoprecipitate. Cryoprecipitate prepared in this way typically contains concentrated within it from 40 to 60% of the total amount of factor VIII contained in the whole blood from which the plasma is derived.

There have been numerous studies to improve the yield of factor VIII from cryoprecipitate and other blood plasma fractions, and to stabilise and further purify it. For example, a minimum purification step is the treatment of cryoprecipitate with Al(OH)$_3$ gels which have been found to eliminate some of the other blood clotting factors, stabilise the activity of factor VIII, and facilitate the subsequent sterile filtration of factor VIII. Usually, however, multi-stage processing of cryoprecipitate is required to produce sufficiently pure FVIII preparations.

The major shortcoming of present technology is that for the most part multi-stage processing of plasma results in rather costly losses of factor VIII activity. In addition, it has long been accepted that commercial preparations of factor VIII vary greatly in terms of anti-haemophilic activity, total protein content, and contamination by other proteins particularly fibrinogen and fibronectin. The presence of high concentrations of fibrinogen and fibronectin in FVIII preparations is undesirable because they have been found to give rise to unacceptable losses of FVII during some of the processing steps. Fibrinogen is of particular concerned because it is normally present in much greater concentrations than fibronectin in blood plasma and cryoprecipitate, and is usually more difficult to remove than fibronectin. Thus, all presently known methods for the purification of factor VIII preparations involve partial separation of fibrinogen at least from factor VIII in order to increase the ratio of factor VIII to total protein content in the preparations.

It has long been accepted that the presence of the proteins fibronectin and especially fibrinogen in blood plasma fractions tend to make those fractions sticky and viscous. This makes purification of these fractions difficult, especially if filtering is used. This problem can to a certain extent be overcome by diluting the fractions in (for example) buffer solutions, though at the expense of loss of plasma fraction concentration. Another serious problem with these proteins arises from the increased need to ensure that all possible blood born viruses, especially the hepatits B virus, the non-A non-B (NANB) hepatitis virus, and the LAV-HTLV III (AIDS) virus, are inactivated before the plasma fraction or blood product isolated therefrom is administered to a patient.

Inactivation of blood-born viruses has traditionally been undertaken by heating plasma fractions or blood products prepared therefrom for extended periods of time. For example, there is clinical evidence that heating freeze-dried (lyophilized) blood products such as freeze-dried FVIII at $60°$ C. for 24 hours is sufficient to inactivate the hepatitis B and AIDS viruses, though there is some evidence that heating to this temperature for as much as 72 hours is not sufficient to guarantee inactivation of the NANB hepatitis virus. The use of moderate-to-high temperatures for extended periods of time does, however, tend to denature any fibrinogen and fibronectin present in the heat-treated product, and these denatured proteins are found to be much more insoluble than those same proteins prior to denaturing. The presence of insoluble products in preparations for intraveneous administration is of course unacceptable, and can lead to an appropriate loss of desirable blood products such as FVIII into these insoluble products even if they are removed after heat treatment. Indeed, so severe is the problem when attempting to purify FVIII from cryoprecipitate that even if 80–90% of the total fibrinogen present in the cryoprecipitate is successfully removed, the problem of protein insolubility in the final FVIII preparation can still be significant, and it has hitherto been very difficult to achieve fibrinogen removal of greater than 80%, especially greater than 90%, from cryoprecipitate without incurring significant losses of FVIII. This problem has become more acute because of the need to consider using even more severe virus inactivation conditions (such as $70°-80°$ C. for 72 hours) to ensure the safety of blood product preparations, which can increase yet further the degree of fibrinogen/fibronectin denaturisation.

U.S. Pat. No. 4406886 (Bier et al) describes one method of purifying factor VIII in which fibrinogen is precipitated from cryoprecipitate preparations by the addition of zinc ions. However cryoprecipitate and other blood plasma fractions usually contain citrate anticoagulants which are added to fresh blood soon after donation and are carried over into the concentrate. Bier et al acknowledge that the concentration of zinc ions required to cause a given precipitation is dependent on citrate ion concentration, and they further acknowledge that the optimum range of zinc ion concentration for a given separation is rather narrow. In practice, because it is often necessary to obtain cryoprecipitate from plasma in different anticoagulants, and since cryoprecipitate as recovered from the centrifuge contains varying amounts of supernatant fluid, citrate ion concentration within the plasma fraction is variable and is usually unknown at the time of zinc addition. This has resulted in considerable difficulty in obtaining consistent results in terms of both separation of fibrinogen and yields of factor VIII. A further problem associated with the method of Bier et al is that the conditions used to obtain optimal yield of Factor VIII leave in the solution concentrations of contaminating fibrinogen and fibronectin which limit the success of further processes, such as heating to inactivate viruses.

An alternative method of separating FVIII, fibrinogen and fibronectin from plasma fractions which at least partly overcomes the problems of the process of Bier et al is described in EP-0022052-A2 (Amrani). This patent is specifically concerned with the separation and recovery of FVIII, fibronectin, and the von Willebrand's factor in high yields from blood plasma. This method includes the steps of precipitating fibrinogen and fibronectin from a blood plasma by adding 0.20 mg of a sulphated mucopolysaccharide (eg heparin) per ml of the plasma, and then cooling the plasma to 2° C. to 4° C. for 3 hours. The patent specification states that the term blood plasma encompasses cryoprecipitate which has been dissolved in dilute salt buffers. Indeed, the use of buffered cryoprecipitate solutions in a similar low temperature precipitation step is described in EP-0127603-A (Eibl et al), in which cryoprecipitate is dissolved in a buffer solution containing 0.1 mg of a sulphated polysaccharide (SPS) per ml of solution, after which the solution is held at 4° C. to allow fibrinogen to precipitate from solution. The precipitate is then removed by centrifugation to yield a supernatant rich in FVIII. The supernatant is subsequently concentrated by precipitation, reconstitution and freeze-drying to yield a stabilised FVIII preparation having a specific activity of at least 1.5 international units (iu) of FVIII per mg of total proteins present in the preparation.

The disadvantage of the above two methods based on sulphated polysaccharide precipitation are that although they demonstrate that such a precipitation is useful to a certain extent in the production of FVIII concentrates, FVIII losses through the multi-stage processing of plasma fractions are still appreciable and/or the concentrates produced still contain significant amounts of unwanted proteins.

It is an object of the present invention to at least partly overcome one or both of these disadvantages by providing an improved method of preparing a FVIII——containing preparation which includes the steps of precipitating fibrinogen and fibronectin from a buffered solution of a FVIII—containing blood plasma fraction by the addition of a sulphated polysacharide (hereinafter referred to as "SPS"), and removing the precipitate from the FVIII—containing supernatant. More specifically, it is an object of the present invention to provide an improved method of preparing a FVIII—containing preparation having an enhanced specific activity of FVIII, comprising the steps of precipitating fibrinogen and fibronectin from a buffered solution of cryprecipitate at pH 6 to 8 by the addition of a SPS, removing the precipitate from the FVIII—containing supernatant, precipitating FVIII from the supernatant with a protein in the presence of salts, redissolving the FVIII precipitate, and converting the redissolved FVIII into a form which can be stored.

The present invention achieves these objects by the addition of at least 0.15 mg of SPS per ml of buffered blood plasma fraction solution whilst maintaining the temperature of the solution, during the precipitation and separation of the fibrinogen and fibronectin, at more than 15° C. The SPS may be added to the plasma fraction solution either with the buffer solution used to make up the buffered blood plasma fraction solution, or, preferably, after the buffered plasma fraction solution has been prepared.

The SPS used in the present invention is preferably a heparinoid such as a mucopolysaccharide polysulphate, pentosan polysulphate, chondroitin sulphate or dextran sulphate, and is most preferably heparin.

Heparin is a complex organic acid containing glucosamine, glucuronic acid and sulphuric acid. It is known to delay the coagulation of blood, and is used, usually by intravenous or subcutaneous injection, in medicine and surgery. It is normally obtained from the lungs or intestinal mucosa of mammals, and in the present invention it is preferably used in the form of a water-soluble alkali metal salt, most preferably its sodium salt.

Hitherto it has not been appreciated that high SPS concentrations together with moderate or high processing temperatures can, in accordance with the present invention, enhance both FVIII recovery and removal of unwanted proteins. The present inventor has discovered that above 15° C., precipitation of firbonectin and especially fibrinogen increases (for a given temperature) with increasing SPS concentration above 0.15 mg/ml plasma fraction solution up to a maximum concentration of about 1.2 mg/ml plasma fraction solution. It has also been discovered that at these high SPS concentrations, supernatants yields of FVIII over the SPS precipitation stage of a FVIII purification process increase steadily as solution precipitation and separation temperatures increase above 10° C., producing highly desirable yields above 15° C.

The degree of fibrinogen and fibronectin precipitation is found to decline somewhat with increasing temperature for a given SPS concentration, due to the increased solubility of these proteins in the supernatant. However, the present inventor has found, surprisingly, that not only can this effect of reduced fibrinogen/fibronectin precipitation at elevated temperature be compensated for by increasing the SPS concentrations in the plasma fraction solution to more than 0.15 mg/ml, preferably to 0.3–0.9 mg/ml, most preferably to 0.44–0.88 mg/ml, but also at these high SPS concentrations high supernatant yields of FVIII can also be maintained. At temperatures above 40° C., fibrinogen and fibronectin solubility becomes a more intractable problem and protein denaturing may occur, and so the temperature of the plasma fraction during precipitation and separation of the fibrinogen/fibronectin precipitate is preferably 20°-35° C., most preferably 25°-30° C.

The upper limit of SPS concentration in the plasma fraction solution is not generally critical. However there is some evidence to suggest that above about 1.2 mg SPS per ml of plasma fraction solution, there is little further improvement in fibrinogen/fibronectin precipitation and slight losses of FVIII yield may occur. For this reason the upper limit of SPS concentration is conveniently 3.0 mg/ml, preferably 2.0 mg/ml.

It has also been discovered that although fibrinogen and fibronectin precipitation efficiency decreases somewhat with increasing precipitation temperature, the loss of fibrinogen precipitation efficiency is, surprisingly, only relatively slight provided a sufficiently high SPS concentration (preferably above 0.30 mg/ml) in the plasma fraction is use. Since fibrinogen is usually present in much higher concentrations than fibronectin in blood plasma fractions, the overall eficiency of unwanted protein precipitation is not, therefore, unduly impaired within certain temperature limits (typically 20°-35° C.). Indeed, it is a particular advantage of the invention that it achieves highly efficient fibrinogen removal in particular, because fibrinogen removal has generally been a more difficult step to achieve in previous FVIII purification processes.

A significant additional advantage of the discovery that efficient unwanted protein removal can be effected above 15° C. is that the amount of buffer solution required to make up the buffered plasma fraction solution for precipitation is normally significantly less than that required in conventional low temperature (2° C.−8° C.) precipitation methods using a SPS. This is mainly due to the fact that FVIII solubility is much higher at temperatures above 15° C., and so the FVIII is capable of remaining in solution at higher FVIII concentrations. Typically, where the plasma fraction is cryoprecipitate the amount of buffer solution used in the present method may be from 1% to 5% of the initial volume of blood plasma from which the cryoprecipitate is extracted, or between 0.5 and 6 parts, preferably between 1 and 3 parts, of buffer solution per part of cryoprecipitate. Cryoprecipitate must normally be diluted with at least 0.5 parts by volume of buffer solution in order to dissolve the cryoprecipitate for further processing.

The advantage of the requirement for relatively small quantities of buffer solution is that the degree of subsequent FVIII concentration, the size of the concentration equipment, and the volume of the reagents required for FVIII concentration will all be reduced for a given output of FVIII. Furthermore, smaller volumes of buffer solution will require smaller volumes of SPS for an equivalent final concentration of SPS in the buffered solution. Thus, although the optimum SPS concentration of 0.44–0.88 mg/ml in the present invention is considerably above the 0.1–0.2 mg/ml concentration conventionally used, these high optimum concentrations can be achieved without using significantly larger quantities of SPS.

A further advantage of the moderate fibrinogen/fibronectin precipitation temperatures used in the present invention is that provided a sufficiently high concentration of SPS is used, precipitation of fibrinogen is maximal after about 5 minutes mixing and no significant further precipitation of factor VIII occurs up to at least 20 minutes. Short reaction times and tolerance of extended holding periods are advantages for large-scale processing.

Factor VIII has a relatively narrow range of pH stability. It is most stable in the neutral pH range of 6.0 to 8.0, hence the pH of the blood plasma fraction is preferably within this range both during and after SPS addition. Blood plasma fraction pH is adjusted using an appropriate buffer solution. Most preferably, however, the pH of the fraction is kept within the range 6.0 to 7.0. Above pH 7.0, useful precipitation of fibrinogen and fibronectin is obtained only at very high SPS concentrations. As pH decreases from pH 7 to pH 6, factor VIII losses into the precipitate increase as precipitation of fibrinogen and fibronectin increase. pH can therefore be easily manipulated by the use of appropriate buffer solutions, to give a range of compromises between factor VIII yield and purity required.

After SPS precipitation has been completed, the precipitate is preferably removed without delay from the supernatent by, for example, centrifugation. The precipitate may be discarded or may be further processed to extract the fibronectin (which is becoming of increasing clinical interest) and the fibrinogen.

SPS precipitation may be used alone to purify a blood plasma fraction or may be used in conjunction with other purification steps as part of a factor VIII purification process.

Where purification consists solely of SPS precipitation, then residual SPS remaining in the supernatant after precipitation may be left in solution or may be removed in part or in full by, for example, the convention step of adsorption onto $Al(OH)_3$ hydrogel. The preparation may then be stabilised and further concentrated by freeze drying, followed by reconstitution in aqueous solution to an appropriate concentration before use.

Where SPS precipitation forms only part of a factor VIII purification process, then this precipitation can be carried out after certain other purification steps. Preferably, however, SPS precipitation is carried out as early as possible in the process, because fibronectin and especially fibrinogen are known to influence other purification steps and so efficient early removal of these contaminants is desirable.

In a commercial factor VIII purification process, SPS precipitation will normally be followed by one or more known concentration steps optionally in conjunction with a pasteurisation step.

Pasteurisation is a especially important step because it inactivates potentially harmful viruses which are transmissible by blood (eg hepatitis viruses) and which are carried over into plasma fraction such as cryoprecipitate. A typical pasteurisation step consists of heat treatment in solution at 60° C. for 10 hours. Large quantities of carbohydrate eg sorbitol and of amino-acids such as glycine are usually added to help stabilise factor VIII at these temperatures, as described in U.S. Pat. No. 4,297,344 (Schwinn et al) and factor VIII yields through pasteurisation are also improved by the addition of small amounts of citrate ions and calcium ions. The presence of residual SPS from the earlier SPS precipitation step is not found to have any significant effect on factor VIII yields through a typical pasteurisation step. After heating, the factor VIII can be removed and concentrated by ultrafiltration or by precipitation with a mixture of an amino acid and a neutral salt (such as glycine and sodium chloride), followed by desalting.

Two other known methods of preparing "heat-treated" concentrates of factor VIII, with the intention of inactivating bloodborne viruses, have been found to be most successful after efficient removal of fibrinogen and fibronectin by precipitation with heparin.

(a) Factor VIII is precipitated from the heparin-containing supernatant by addition of high concentrations of a amino acid/neutral salt mixture (such as glycine and sodium chloride), and the precipitate redissolved in a small volume of buffer solution. After desalting by (for example) gel filtration, the solution is sterilised, freeze-dried and heated in its final container to temperatures of at least 70° C. for at least 24 h with little or no loss of factor VIII activity or solubility.

(b) The factor VIII, reprecipitated and redissolved as in (a), is pasteurised in solution after the addition of high concentrations of an amino acid and a carbohydrate (eg glycine and sorbitol) by the method of Schwinn et al. The heated factor VIII is then recovered by ultrafiltration or by a second precipitation with an amino acid/neutral salt mixture, followed by desalting.

Methods of precipitating fibrinogen and fibronecting from blood plasma fractions in accordance with the present invention will now be described by way of example only.

MATERIALS

The following materials were used in the Examples
1. Heparin.

The heparin used was porcine intestinal mucosal heparin in the form of US Pharmacopoeia (USP) Grade 1 sodium heparin supplied by Sigma Chemical Co, St Louis USA having a specific activity of about 168 units (u) per milligram. The heparin was made up into a standard stock solution having a heparin concentration of 3750 u/ml (22 mg/ml). Other sources of heparin USP may also be used.

GENERAL PROCEDURES

The following general procedures were used in the Examples

1. Method of preparing cryoprecipitate

Whole blood anticoagulated with sodium citrate anticoagulant was centrifuged within a few hours of donation and the separated plasma frozen to $-25°$ C. to $-40°$ C. in plastic containers. Before cryoprecipitation proper, the frozen plasma was softened to $-5°$ C. to $-15°$ C. by storage for several hours in a room at $0°-5°$ C., and the thawing process was facilitated by breaking up the frozen plasma. The pieces of frozen plasma were warmed in a jacketed vessel under efficient manual or mechanical stirring, so that no part of the suspension rose above a temperature of about $+3°$ C. to prevent the desired cryoprecipitate from redissolving in the liquid phase. Ideally, the suspension was kept at $+1°$ C. The cryoprecipitate was separated from the partly thawed suspension by continuous centrifugation in a Sharples continous tubular centrifuge maintained at about $+1°$ C. to $+3°$ C. The cryoprecipitate was redissolved by mixing at $20°$ C.$-25°$ C. with a volume of 20 mM tris-HCl buffer, pH 6.8, equivalent to 2.4% of the volume of the plasma taken, and the solution was used fresh or was stored frozen at $-30°$ C. for later use.

2. Method of precipitating fibrinogen and fibronectin using heparin

Cryoprecipitate solution was thawed to about 25° C. and was taken either undiluted or, in some Examples, diluted with up to one volume of 20 mM tris pH 6.8. The pH of the thawed cryoprecipitate was adjusted to a desired level if necessary by mixing in small quantities of either 0.1M or 0.05M HCl. Stock heparin solution was then added in a rapid stream by pipette or syringe whilst continuously stirring the mixture. After thorough mixing the suspension containing fibrinogen and fibronectin precipitate was centrifuged at 4000 xg for 10 minutes, and the supernatant poured off. All steps were performed at about 25° C.

ASSAYS

The following assay techniques were employed on the blood plasma concentrates both before and after conducting the methods described in the Examples, in order to determine yields of various components in the concentrates.

1. Factor VIII

Two-stage Factor VIII Coagulant (factor VIIIC) assays were done usually on frozen but occasionally on fresh samples. Heparin-containing samples were routinely absorbed with 0.1 volume of $Al(OH)_3$ (Al hydrogel) for 3 minutes at 37° C. in order to remove the heparin before assay.

2. Total protein and fibrinogen

Total protein was assayed by the biuret method. Fibrinogen was measured as the component of the protein which was clottable with thrombin.

3. Fibronectin

Fibronectin was assayed by Laurell immunoelectrophoresis.

4. Heparin

Heparin was assayed by the inhibition of factor Xa activity, measured by the rate of hydrolysis of the synthetic substrate S-2222 (Tein A N, Lie, M and Abildgaard, U. Thrombosis Research, 8, 413, 1976).

EXAMPLES 1-7

The above general procedure was used to precipitate fibrinogen and fibronectin from undiluted aliquots of the same cryoprecipitate solution, by adding heparin to the solution to a final concentration value of either 0.31 or 0.44 mg/ml solution after adjusting the pH of the solution to between pH 5.8 and 7.1. The resulting mixtures were centrifuged after five minutes of heparin addition. The results of heparin precipitation in terms of yields of factor VIII:C, fibrinogen and fibronectin in the supernatant are given in Table 1 below.

TABLE 1

| Example | Heparin added mg/ml | Supernatant pH | % yields in supernatant | | |
|---|---|---|---|---|---|
| | | | Factor VIII:C | Fibrinogen | Fibronectin |
| 1 | 0.44 | 5.8 | 42 | 10 | 0 |
| 2 | 0.44 | 6.4 | 65 | 7 | 15 |
| 3 | 0.44 | 6.5 | 70 | 8 | 16 |
| 4 | 0.44 | 6.6 | 68 | 12 | 20 |
| 5 | 0.44 | 6.7 | 66 | 15 | 27 |
| 6 | 0.31 | 6.5 | 69 | 11 | 42 |
| 7 | 0.31 | 7.1 | 72 | 30 | 74 |

From these and similar experiments at other pH values and heparin concentrations, it was established that the precipitation of fibronogen and fibronectin tended to increase as pH was reduced, at the cost of increasing loss of factor VIII, with a preferred compromise at about pH 6.5.

EXAMPLES 8 TO 13

Using the above general procedure, fibrinogen/fibronectin precipitation was performed on samples of between 5 ml and 1500 ml of thawed cryoprecipitate solution extracted from various blood plasma sources, some of which were diluted with one volume of 0.02M tris pH 6.8. pH was adjusted to 6.55±0.03 by the addition of HCl solution. Heparin was then admixed to each sample to a final concentration value of between 0.22 mg/ml and 0.88 mg/ml to effect fibronectin and fibrinogen precipitation. The resulting mixture was centrifuged after 5 minutes of heparin addition. The results of heparin precipitation in terms of yields of factor VIIIC, fibrinogen, and fibronectin are given in Table 2 below.

TABLE 2
(Effect of cryoprecipitate dilution)

| Example | Volume of 0.02 M tris added | Heparin added mg/ml | Number of experiments performed n | % yields in supernatant* F VIII:C | Fibrinogen | Fibronectin |
|---|---|---|---|---|---|---|
| 8 | 0 | 0.22 | 17 | 78 ± 7 | 19 ± 3 | 51 ± 12 |
| 9 | 0 | 0.44 | 9 | 75 ± 11 | 10 ± 3 | 29 ± 6 |
| 10 | 0 | 0.88 | 1 | 56 | 4 | 11 |
| 11 | 1 | 0.22 | 6 | 75 ± 6 | 7 ± 2 | 28 ± 3 |
| 12 | 1 | 0.44 | 1 | 68 | 6 | 31 |
| 13 | 1 | 0.67 | 1 | 65 | 9 | 35 |

*standard deviations from mean yields are given where n >1.

The above Table 2 shows that fibrinogen and fibronectin removal increase with increasing heparin concentration. Dilution of cryoprecipitate solution with tris buffer (ie reduction of protein concentration) permits more efficient removal of fibrinogen and fibronectin, with good factor VIII yield, at lower heparin concentrations. On an industrial scale, however, it is preferable to avoid dilution of the cryoprecipitate solution and to use a heparin concentration of about 0.66 mg/ml, giving excellent separation of factor VIII from fibrinogen and fibronectin similar to that achieved in diluted solution at 0.44 mg heparin/ml.

EXAMPLES 14 TO 18

The above general procedure was used to effect fibrinogen/fibronectin preicipitation from 10 ml samples of cryoprecipitate solution, each taken from the same blood plasma source. The pH of each sample was adjusted to pH 6.55±0.03 by the addition of HCl solution. Heparin was then admixed to each sample to a final concentration value of between 0.22 mg/ml and 0.88 mg/ml to effect fibronectin and fibrinogen precipitation. The resulting mixture was centrifuged after 5 minutes. The results of heparin precipitation in terms of yields of factor VIIIC, fibrinogen, and fibronectin are given in Table 3 below.

TABLE 3
(Effect of heparin concentration)

| Example | Heparin added mg/ml | % yields in supernatant Factor VIII:C | Fibrinogen | Fibronectin |
|---|---|---|---|---|
| 14 | 0.22 | 67 | 29 | 37 |
| 15 | 0.33 | 68 | 16 | 20 |
| 16 | 0.44 | 69 | 11 | 16 |
| 17 | 0.66 | 75 | 6 | 20 |
| 18 | 0.88 | 67 | 3 | 13 |

The above Table 3 shows that, with increasing heparin concentration, precipitation of fibrinogen and fibronectin tends to increase but the yield of Factor VIII remains relatively constant.

EXAMPLES 19 (Comparative)

The method of Example 6 was repeated on nine separate samples of thawed cryoprecipitate using zinc ions at a concentration of 1.5 mM in the cryoprecipitate instead of heparin, producing yields (±standard deviations) of 71±9% factor VIIIC, 24±5% fibrinogen, and 51±8% fibronectin in the supernatant. These results compare unfavourably with those of Examples 2 to 6 above both in terms of factor VIIIC yield and in terms of the quantities of fibrinogen and fibronectin precipitated. The high levels of fibrinogen and fibronectin left in solution have a marked influence on the properties, especially the solubility, of the concentrates obtained by further processing eg pasteurisation or heating in the freeze-dried state.

EXAMPLES 20-22

10 ml samples of cryoprecipitate solution were subjected to fibrinogen/fibronectin precipitation and centrifuge separation in acordance with the above general procedures, except that temperatures other than 25° C. were used. In each Example the amount of heparin added was 0.73 mg/ml cryoprecipitate solution, and the pH of the solution was maintained at 6.55±0.05. The results in terms of protein yields in the supernatant are given in Table 4 below.

TABLE 4
(Effect of Temperature)

| Example | Cryoprecipitate Solution Temperature (°C.) | % yields in supernatant Factor VIII:C | Fibrinogen | Fibronectin |
|---|---|---|---|---|
| 20 | 10 | 22 | 4.2 | 6.2 |
| 21 | 20 | 73 | 5.3 | 21 |
| 22 | 30 | 91 | 7.7 | 27 |

Example 20 is included for the purpose of comparison only.

EXAMPLE 23 (comparative)

4.9 g of cryoprecipitate recovered from 594 ml of blood plasma, was mixed for 20 minutes at 20° C. in 62 ml of a pH 6.7 buffer solution containing 20 mM Na$_3$ citrate, 0.1 mg/ml sodium heparin (Sigma Grade 1) and 30 u/ml aprotinin (Trasylol, Bayer AG). The protein content of the resulting suspension per kg of the plasma from which the cryoprecipitate was extracted was found to be 355 iu FVIII:C, 607 mg fibrinogen and 355 mg fibronectin. The content of FVIII:C in the suspension was, specifically, 3.1 iu FVIII:C per ml at a specific activity of FVIII:C of 0.36 iu/mg total proteins, 0.58 iu/mg fibrinogen and 1.00 iu/mg fibronectin. The resulting solution was adjusted to pH 6.3 by the addition of 0.1M HCl solution, and was then coled to +4° C. and held at that temperature for 5 minutes to effect precipitation of fibrinogen and fibronectin. The precipitate was removed by centrifuging the mixture at 4° C. for 10 minutes at 4000 xg. The supernatant was then poured off.

The yield of FVIII:C, fibrinogen and fibronectin in the supernatant was measured at 66%, 25.5%, and 19% respectively of the concentrations of these proteins in the buffered solution prior to precipitation, and the specific activity of FVIII:C in the supernatant was calculated at 0.62 iu/mg total proteins, 1.50 iu/mg fibrinogen, and 3.50 iu/mg fibronectin.

FVIII:C was recovered from the supernatant by conventional precipitation using a saline, 2.2M glycine solution. The precipitate was recovered by centrifugation as before and was then redissolved in a pH 6.9 Tris/citrate/chloride buffer solution. The redissolved precipitate was found to have retained 99% of the FVIII:C, 91% of the fibrinogen, and 26% of the fibronectin that had been present in the supernatant prior to FVIII:C precipitation. The FVIII:C specific activity in the redissolved precipitate was calculated at 1.37 iu/mg total proteins, 1.64 iu/mg fibrinogen, and 13.2 iu/mg fibronectin.

EXAMPLE 24

2665 g of cryoprecipitate, recovered from 323 liters of blood plasma, was dissolved with mixing for 20 minutes at 20° C. in 7.75 liters of a pH 6.7, 20 mM Tris buffer solution. The protein content of the resulting solution per kg of the plasma from which the cryoprecipitate was extracted was found to be 388 iu FVIII:C, 793 mg fibrinogen and 269 mg fibronectin. The content of FVIII:C in the solution was found to be 11.7 iu/ml at a specific activity of FVIII:C of 0.30 iu/mg total proteins, 0.49 iu/mg fibrinogen and 1.44 iu/mg fibronectin. The resulting buffered solution was adjusted to pH 6.55 at 25° C. by the addition of 0.1M HCl solution, and to the solution was then added a 22 mg/ml concentrated stock solution of sodium heparin (Sigma Grade 1) until the concentration of sodium heparin in the buffered solution reached 0.66 mg/ml solution. The heparin solution was added in a rapid stream whilst continuously stirring the mixture, and after 5 minutes of thorough mixing the fibrinogen/fibronectin precipitate which had formed was removed by centrifuging the mixture, still at 25° C., for 10 minutes at 4000 xg. The supernatant was then poured off.

The yield of FVIII:C, fibrinogen and fibronectin in the supernatant was measured at 92%, 7.3%, and 27% respectively. The specific activity of FVIII:C in the supernatant was calculated at 0.87 iu/mg total proteins, 6.21 iu/mg fibrinogen, and 4.92 iu/mg fibronectin.

FVIII:C was recovered from the supernatant by precipitation and then redissolved in a more concentrated form by an identical procedure to that outlined in Example 23. The redissolved precipitate was found to have retained 89% of the FVIII:C, 83% of the fibrinogen, and 17% of the fibronectin that had been present in the supernatant prior to FVIII:C precipitation. The FVIII:C specific activity in the redissolved precipitate was calculated at 4.86 iu/mg total proteins, 6.88 iu/mg fibrinogen, and 25.7 iu/mg fibronectin.

In order to prepare FVIII:C preparations suitable for clinical use, the above redissolved FVIII:C solution was desalted by gel filtration, sterilised by membrane filtration, dispensed as 10 ml aliquots into vials, and then lyophilized. In order to inactivate any blood-born viruses present in the lyophilised preparations, the vials were heated in an oven at 80° C. for 72 hours. After reconstitution by the addition of 10 ml of distilled water to each vial, the preparations were found to be fully dissolved and ready for use within 5 minutes. On average, 90% of the FVIII:C activity present before heating to 80° C. was found to be present in the reconstituted preparations.

I claim:

1. A method of preparing a FVIII-containing preparation which includes the steps of precipitating fibrinogen and fibronectin from a buffered solution of FVIII-containing blood plasma fraction by the dissolution of a SPS, and removing the precipitate from the FVIII-containing supernatant, characterised in that the amount of SPS added to the plasma fraction is at least 0.15 mg of SPS per ml of the buffered solution and further characterised in that the temperature of the buffered solution during the precipitation and removal of the fibrinogen and fibronectin is maintained at more than 15° C.

2. A method according to claim 1 characterised in that the amount of SPS added to the plasma fraction is not more than 3.0 mg of SPS per ml of the buffered solution.

3. A method according to claim 2 characterised in that the amount of SPS added to the plasma fraction is from 0.3 to 1.2 mg per ml of the buffered solution.

4. A method according to claim 3 characterised in that the amount of SPS added to the plasma fraction is from 0.44 to 0.88 mg per ml of the buffered solution.

5. A method according to claim 1 characterised in that the temperature of fibrinogen and fibronectin precipitation and removal is maintained at not more than 40° C.

6. A method according to claim 5 characterised in that the temperature of fibrinogen and fibronectin precipitation and removal is maintained at 20° C. to 35° C.

7. A method according to claim 6 characterised in that the temperature of fibrinogen and fibronectin precipitation and removal is maintained at 25° C. to 30° C.

8. A method according to claim 1 characterised in that the pH of the buffered solution is from 6.0 to 7.0.

9. A method according to claim 1 characterised in that the SPS is a heparinoid selected from mucopolysaccharide polysulphates, pentosan polysulphate, chondroitin sulphate and dextran sulphate.

10. A method according to claim 9 characterised in that the SPS is heparin or a soluble alkali metal salt thereof.

11. A method of preparing a FVIII-containing preparation having an enhanced specific activity of FVIII, comprising the steps of precipitating fibrinogen and fibronectin from a buffered solution of cryoprecipitate at pH 6 to 8 by the dissolution of a SPS, removing the precipitate from the FVIII-containing supernatant, precipitating FVIII from the supernatant with a protein precipitant in the presence of salts, re-dissolving the FVIII precipitate, and converting the redissolved FVIII into a form which can be stored, characterised in that the amount of SPS added to the cryoprecipitate is at least 0.15 mg of SPS per ml of the buffered solution and further characterised in that the temperature of the buffered solution during the precipitation and removal of the fibrinogen and fibronectin is maintained at more than 15° C.

12. A method according to claim 11 characterised in that the amount of SPS added to the cryoprecipitate is not more than 3.0 mg of SPS per ml of the buffered solution.

13. A method according to claim 12 characterised in that the amount of SPS added to the cryoprecipitate is from 0.3 to 1.2 mg per ml of the buffered solution.

14. A method according to claim 13 characterised in that the amount of SPS added to the cryoprecipitate is from 0.44 to 0.88 mg per ml of the buffered solution.

15. A method according to claim 11 characterised in that the temperature of fibrinogen and fibronectin precipitation and removal is maintained at not more than 40° C.

16. A method according to claim 15 characterised in that the temperature of fibrinogen and fibronectin precipitation and removal is maintained at 20° C. to 35° C.

17. A method according to claim 16 characterised in that the temperature of fibrinogen and fibronectin precipitation and removal is maintained at 25° C. to 30° C.

18. A method according to claim 11 characterised in that the pH of the buffered solution is from 6.0 to 7.0.

19. A method according to claim 11 characterised in that the SPS is a heparinoid selected from mucopolysaccharide polysulphates, pentosan polysulphate, chondroitin sulphate and dextran sulphate.

20. A method according to claim 19 characterised in that the SPS is heparin or a soluble alkali metal salt thereof.

21. A method according to claim 11 characterised in that the buffered solution of cryoprecipitate is prepared by mixing with cryoprecipitate a volume of a buffer solution equal to 1% to 5% that of the blood plasma from which the cryoprecipitate is extracted.

22. A method according to claim 11 characterised in that the buffered solution of cryoprecipitate is prepared by mixing 1 part cryoprecipitate with 0.5 to 6 parts of a buffer solution.

23. A method according to claim 22 characterised in that the buffered solution of cryoprecipitate is prepared by mixing 1 part cryoprecipitate with 1 to 3 parts of the buffer solution.

* * * * *